US 6,740,873 B2

(12) United States Patent
Pusterla et al.

(10) Patent No.: US 6,740,873 B2
(45) Date of Patent: May 25, 2004

(54) METHOD FOR MEASURING THE CONCENTRATION OF NITROGEN IN ARGON BY MEANS OF ION MOBILITY SPECTROMETRY

(75) Inventors: Luca Pusterla, Milan (IT); Robert Stimac, Palm Beach Gardens, FL (US); Antonio Bonucci, Milan (IT); Marco Succi, Milan (IT)

(73) Assignee: Saes Getters S.p.A., Milan (IT)

( * ) Notice: Subject to any disclaimer, the term of this patent is extended or adjusted under 35 U.S.C. 154(b) by 0 days.

(21) Appl. No.: 10/439,888

(22) Filed: May 16, 2003

(65) Prior Publication Data

US 2003/0201388 A1 Oct. 30, 2003

Related U.S. Application Data

(63) Continuation of application No. PCT/IT01/00561, filed on Nov. 8, 2001.

(30) Foreign Application Priority Data

Nov. 17, 2000 (IT) ........................... MI2000A2479

(51) Int. Cl.⁷ ........................... B01D 59/44; H01J 49/00
(52) U.S. Cl. ..................... 250/281; 250/282; 250/286
(58) Field of Search ................... 250/281, 282, 250/286

(56) References Cited

U.S. PATENT DOCUMENTS

| 4,551,624 A | 11/1985 | Spangler et al. |
| 5,032,721 A | 7/1991 | Bacon et al. |
| 5,095,206 A | 3/1992 | Bacon, Jr. et al. |
| 5,238,199 A | 8/1993 | Ossoinig et al. |
| 5,457,316 A | 10/1995 | Cohen et al. |
| 5,789,745 A | 8/1998 | Martin et al. |
| 5,902,561 A | 5/1999 | Carrea et al. |
| 5,955,886 A | 9/1999 | Cohen et al. |

FOREIGN PATENT DOCUMENTS

GB 2 177 079 A 1/1987

OTHER PUBLICATIONS

Hunter, E.J., et al., "Detection of trace nitrogen in bulk argon using proton transfer reactions," *J. Vac. Sci. Technol.*, Section A, vol. 16, No. 5, pp. 3127–3130 (1998).

Primary Examiner—John R. Lee
Assistant Examiner—Erin-Michael Gill
(74) Attorney, Agent, or Firm—Akin Gump Strauss Hauer & Feld L.L.P.

(57) ABSTRACT

A method for carrying out nitrogen analysis by ionization mobility spectroscopy at concentrations of few parts per billion (ppb) in argon is described. The method involves the addition of hydrogen in concentration of at least 5 ppb and lower than 100 parts per million (ppm) to the argon to be analyzed; the hydrogen addition step may be preceded by a purification operation of the argon flow to reduce the total concentration of impurities other than nitrogen to under 1 ppb.

18 Claims, 11 Drawing Sheets

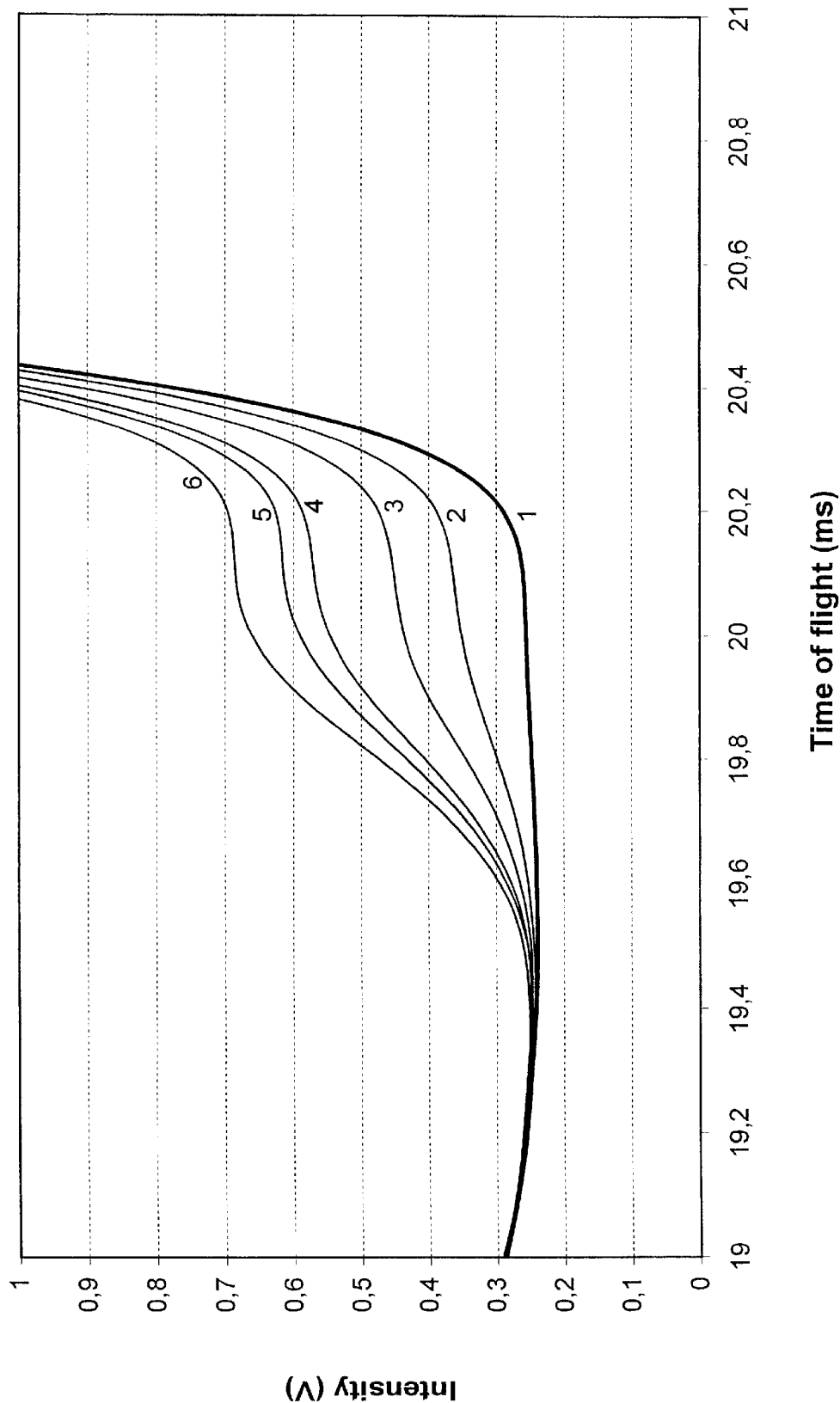
Fig. 4.a

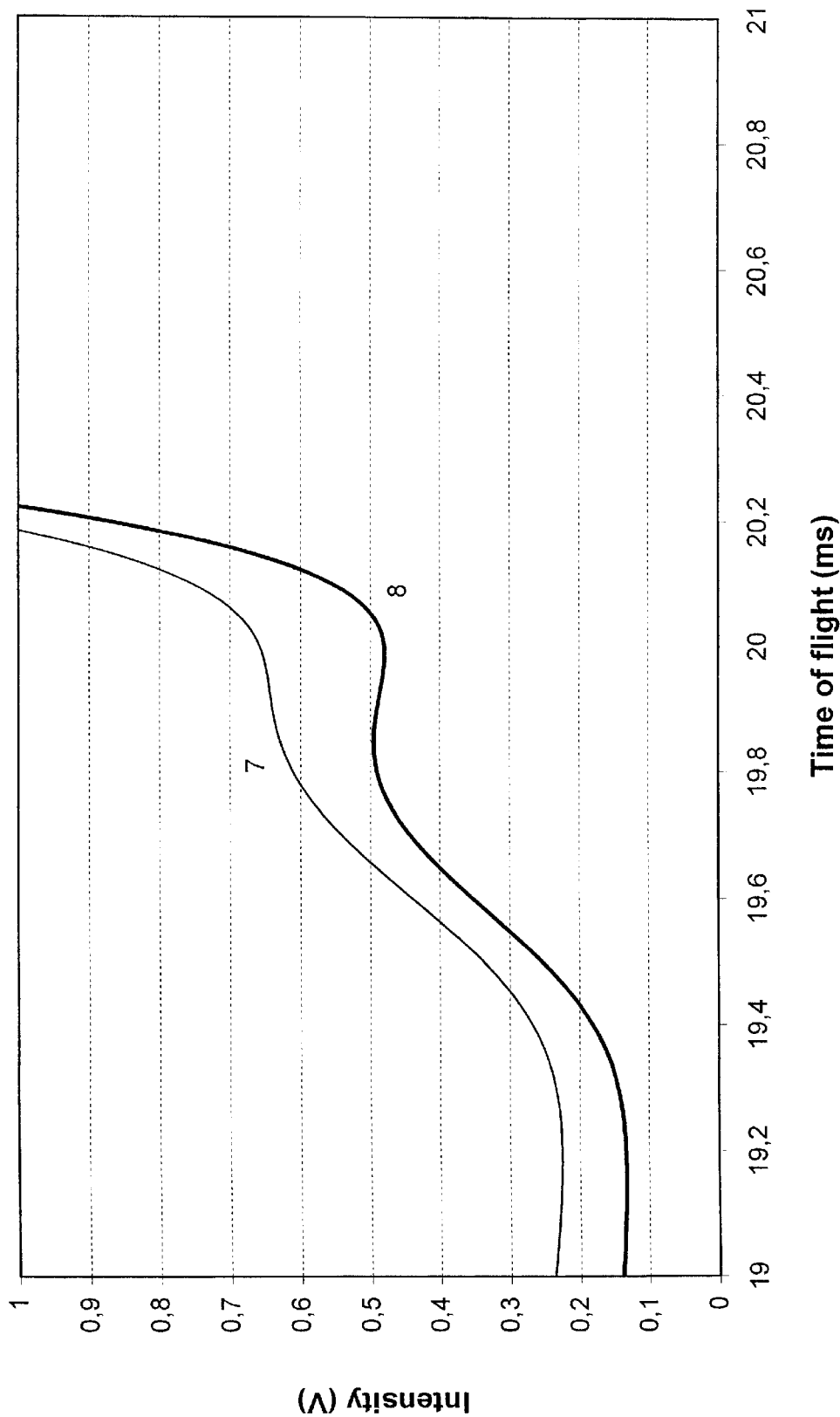
Fig. 5.a

METHOD FOR MEASURING THE CONCENTRATION OF NITROGEN IN ARGON BY MEANS OF ION MOBILITY SPECTROMETRY

CROSS-REFERENCE TO RELATED APPLICATIONS

This application is a continuation of International Application No. PCT/I01/00561 filed Nov. 8, 2001, the disclosure of which is incorporated herein by reference.

BACKGROUND OF THE INVENTION

The present invention relates to a method for measuring the concentration of nitrogen in argon by means of ionization mobility spectroscopy.

Argon is widely used in the semiconductor industry, both as a transport gas wherein reactive species are diluted, and as a support gas for plasma formation in cathodic deposition processes (better known in the field with the definitions of "sputtering" or "Physical Vapor Deposition", PVD). The purity of the employed argon is very important; as a matter of fact contaminants possibly present in the reagents or in the reaction environment can be incorporated into the solid state devices, altering the electrical or magnetic properties thereof and thus giving rise to production wastes.

Argon purification is the subject-matter of a number of patents, including for example patent GB-B-2,177,079 in the applicant's name. According to this patent, argon is purified by passing it through a bed of a getter material (an alloy based on zirconium, vanadium and iron) kept at a temperature between 350 and 450° C. By this method the content of impurities in the argon is reduced below 1 part per billion (ppb, equivalent to one molecule of impurities per $10^9$ argon atoms).

In these conditions, it is also necessary to have the possibility of checking the gas purity and its consistency in time, so as to detect increases of impurity concentration, due for example to anomalies in the operation of the purifiers, loss of tightness of the gas lines or the like.

A particularly interesting technique for carrying out this analysis is ionization mobility spectroscopy, better known in the field with the abbreviation IMS (the same abbreviation is used also for the instrument with which the technique is carried out, in this case indicating "Ionization Mobility Spectrometer"). The interest in this technique derives from its high sensitivity, associated with the limited size and cost of the instrument; by operating in appropriate conditions it is possible to sense gas or vapor phase species in a gaseous medium in quantities of the range of picograms (pg, that is $10^{-12}$ grams), or in concentrations of the order of parts per trillion (ppt, equivalent to a molecule of analyzed substance per $10^{12}$ gas molecules of the sample). IMS instruments and the methods of analysis employing these are described, e.g., in U.S. Pat. Nos. 5,457,316 and 5,955,886 in the name of U.S. company PCP Inc.

An IMS instrument is essentially formed of a reaction zone, a separation zone and a detector of charged particles.

In the reaction zone takes place the ionization, commonly by means of beta-radiations emitted by $^{63}Ni$, of the sample comprising the gases or vapors to be analyzed in a transport gas. Due to the ratio between the number of molecules of the main gas and the impurities therein, the first ionization acts essentially take place on the former, with the formation of the so-called "reagent ions": the charge of these ions is then distributed to the other present species as a function of their electronic or proton affinities or of their ionization potentials. For an illustration of the (rather complex) charge transfer principles which are the base of the ionization mobility spectrometry technique, reference can be made to the book "Ion Mobility Spectrometry" by G. A. Eicen an and Z. Karpas, published in 1994 by CRC Press.

The reaction zone is divided from the separation zone by a grid which, kept at a suitable potential, prevents the ions produced in the former zone from entering into the latter zone. The moment when the grid potential is annulled, thus allowing the entrance of the ions in the separation zone, is the "time zero" of the analysis. The separation zone comprises a series of electrodes which create an electric field such that the ions are carried from the reaction zone towards the detector. This zone is kept at atmospheric pressure. Therefore, the velocity of motion of the ions depends on the electric field and on the crosssection thereof in the gaseous medium. By registering the reading of current of the particle detector as a function of the time passed from the "time zero," peaks corresponding to the so-called "time of flight" of the different ions are obtained. From the determination of the time of flight, it is possible to go back to the presence of the substance, object of the analysis.

In spite of its conceptual simplicity, the application of the technique involves some difficulties in the interpretation of the analysis results.

The instrument, similarly to chromatographs, provides as result of the analysis the crossing time (time of flight in the case of the IMS) of the present species, but does not provide further indications of the chemical nature of the species corresponding to each peak.

For attributing each peak to a chemical species, the IMS may be connected to a mass spectrometer, which determines the chemical nature of each ion, but in this way the above mentioned advantages of low cost and compactness are lost.

Alternatively, it is possible to run calibration tests on samples formed of an extremely pure transport gas containing a substance to be subsequently analyzed, thus determining the time of flight of the molecules of interest. The analysis under real conditions is, however, complicated due to the simultaneous presence of more substances, giving rise to various ionic species which nay lead to phenomena of charge transfer among each other or with present neutral molecules, so that the times of flight found in the analysis can be characteristic of species different from those whose presence is to be determined. In the particular case of the analysis of traces of nitrogen in argon, this is essentially impossible to carry out directly, because the charge transfer among the $Ar^+$ ions (the first ionization product) and nitrogen is scarcely efficient.

In order to overcome the problems found in the real analyses, it has been developed the method of adding the sample gas with a specific substance, called "doping gas" which, according to various mechanisms, obtains the effect of notably increasing the sensitivity of the measure towards the specific molecule object of the analysis.

As examples of practical application of the method of the doping gas may be mentioned U.S. Pat. No. 4,551,624, regarding the addition of ketones or halogenated gases to the gas to be analyzed; U.S. Pat. Nos. 5,032,721 and 5,095,206 regarding, respectively, the use of phenols and sulphur dioxide in the analysis of acid gases; and U.S. Pat. No. 5,238,199, regarding the use of amines in the analysis of chlorine dioxide.

In the specific literature of the IMS field, however, there are no examples of the use of a doping gas for measuring nitrogen in argon. From the paper "Detection of trace nitrogen in bulk argon using proton transfer reactions", by E. J. Hunter et al., (*Journal of Vacuum Science and Technology*, section A, vol. 16, No. 5 of September-October 1998, pages 3127–3130) it is known that the addition of hydrogen in concentrations up to 2—3% increases the sensitivity of an analysis of nitrogen in argon carried out with the technique of mass spectrometry with chemical ionization at atmospheric pressure (technique known, like the relevant instrument, with the abbreviation APCI-MS). This technique provides results which are intrinsically simpler to interpret than the IMS technique, because the detector is a mass spectrometer, which distinguishes the ions present in the sample on the base of the mass/charge ratio thereof, and therefore directly attributes the chemical nature to each measured signal. Besides, the content of this article includes a method for the calibration of the APCI-MS instrument with pure gases, at most containing traces of gases which have to be subsequently analyzed. The teachings of this paper however, if applied straightforwardly, do not allow the IMS measure of nitrogen in argon; as the inventors have observed. By using the very same system described in the article above in an IMS analysis, the measure of nitrogen is quantitatively unreliable, and, in the worst cases, the analysis output is a null reading of nitrogen also in the presence of this gas in the sample, so that even the simple qualitative analysis is impossible.

BRIEF SUMMARY OF THE INVENTION

An object of the present invention is to provide a method for measuring the concentration of nitrogen in argon by means of ionization mobility spectroscopy.

This object is achieved according to the present invention by a method comprising the steps of:

providing an argon flow sample to be analyzed comprising a total concentration of impurities other than nitrogen not higher than about 1 ppb;

adding a quantity of hydrogen to the argon flow sample to be analyzed to produce a mixture of gases comprising a hydrogen concentration between 0.005 and 100 parts per million by volume; and analyzing the mixture of gases with an ion mobility spectroscopy analyzer.

Analogously to what was reported in the cited article by E. J. Hunter et al., the reaction of charge transfer at the base of the measure is believed to be the following:

$$ArH^+ + N_2 \rightarrow N_2H^+ + Ar \quad (I)$$

The studies of the reactions which take place in an IMS chamber have demonstrated that the species really present are more complex than the above reported ones, and generally consist in complex aggregates of ions and neutral molecules. For example, in the method according to the present invention, species of the type $(Ar)_nH^+$, $(Ar)_p(N_2)_qH^+$ and $(H_2O)_r(Ar)_sH^+$ are involved, where n, p, q, r and s are integer numbers. However, "simplified" formulas will be used in the following for the sake of simplicity; some simplified formulas corresponding to the above mentioned species and used in the following are, respectively, $ArH^+$, $N_2H^+$, $(H_2O)_2H^+$ and $H_3O^+$.

BRIEF DESERTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

DETAILED DESCRIPTION OF THE INVENTION

The inventors have found that the measure of the quantity of nitrogen in argon is possible with reliable and reproducible results if, before adding hydrogen, the total amount of gases or vapors other than nitrogen in the argon flow is lower than 1 ppb. This condition can always be satisfied by passing the argon flow under analysis through a suitable purifier (or purification system comprising more than one purifier), as detailed in the following. In the alternative, it is possible to subject the argon flow whose nitrogen content is to be evaluated to a preliminary test. If this trial test determines that the argon flow already meets the purity requirement above, such flow is directly subjected to hydrogen addition and actual IMS analysis, otherwise it is subjected to a purification operation before hydrogen addition.

Figure 1:
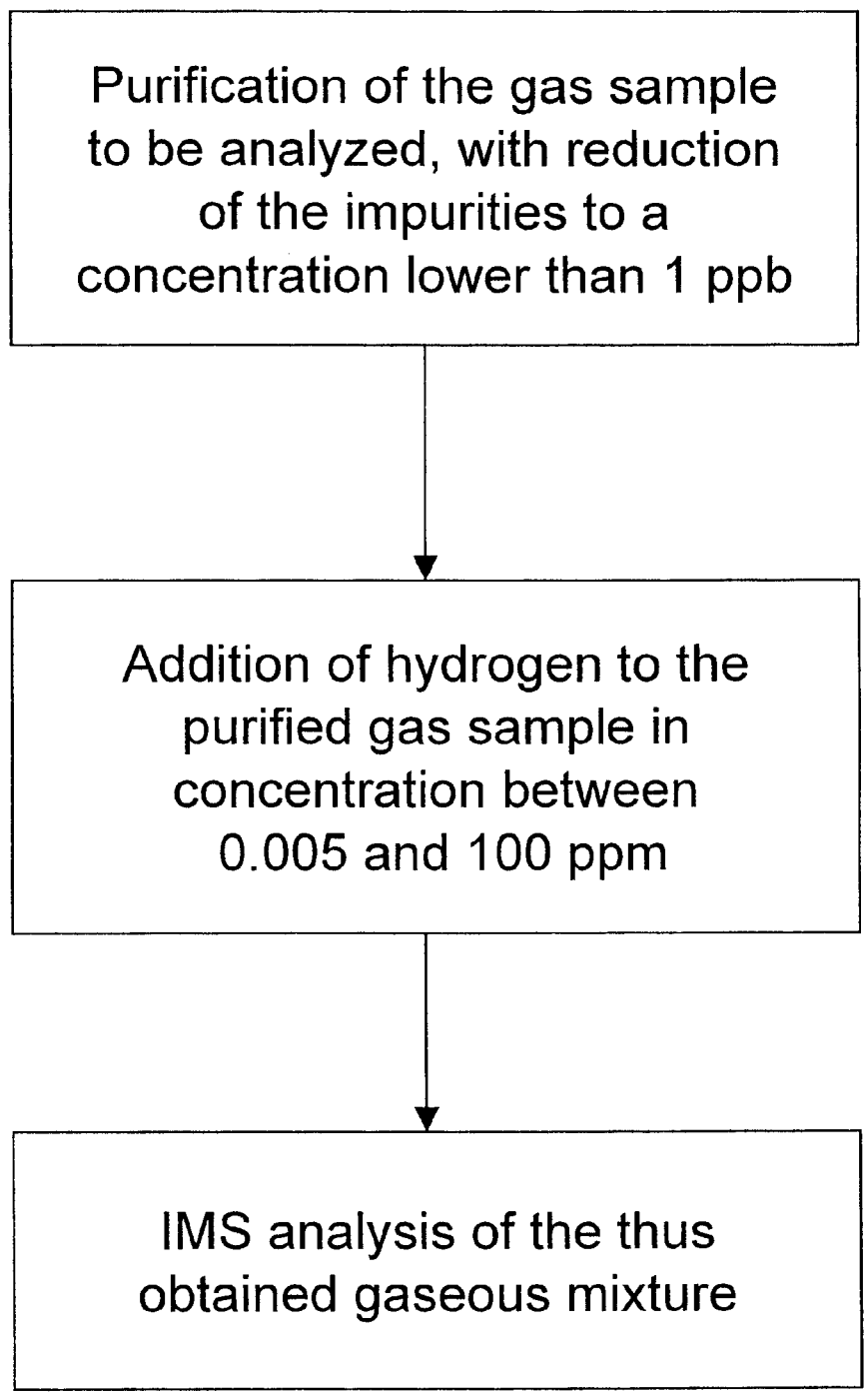
FIG. 1 is a flow diagram showing the essential steps of a first embodiment of the method of the invention.

FIG. 1 shows the steps of the method of the invention in a first embodiment thereof. In this embodiment, the argon flow to be analyzed is passed through a purifier or a purification system irrespective of its original purity, to assure that it has the purity level required for the analysis according to the invention. In this first embodiment, in case the gas entering the system is pure enough already, the purification operation is redundant and increases the overall analysis time; the need for a preliminary trial analysis is however avoided. To the argon flow coming from the purification step is added hydrogen (as specified in the following) so as to obtain a gas mixture containing the same concentration of nitrogen as in the original argon flow, hydrogen in the range from 0.005 to 100 ppm by volume (ppmv in the rest of the text), balance argon This mixture is then fed to the IMS analyzer.

Figure 2:
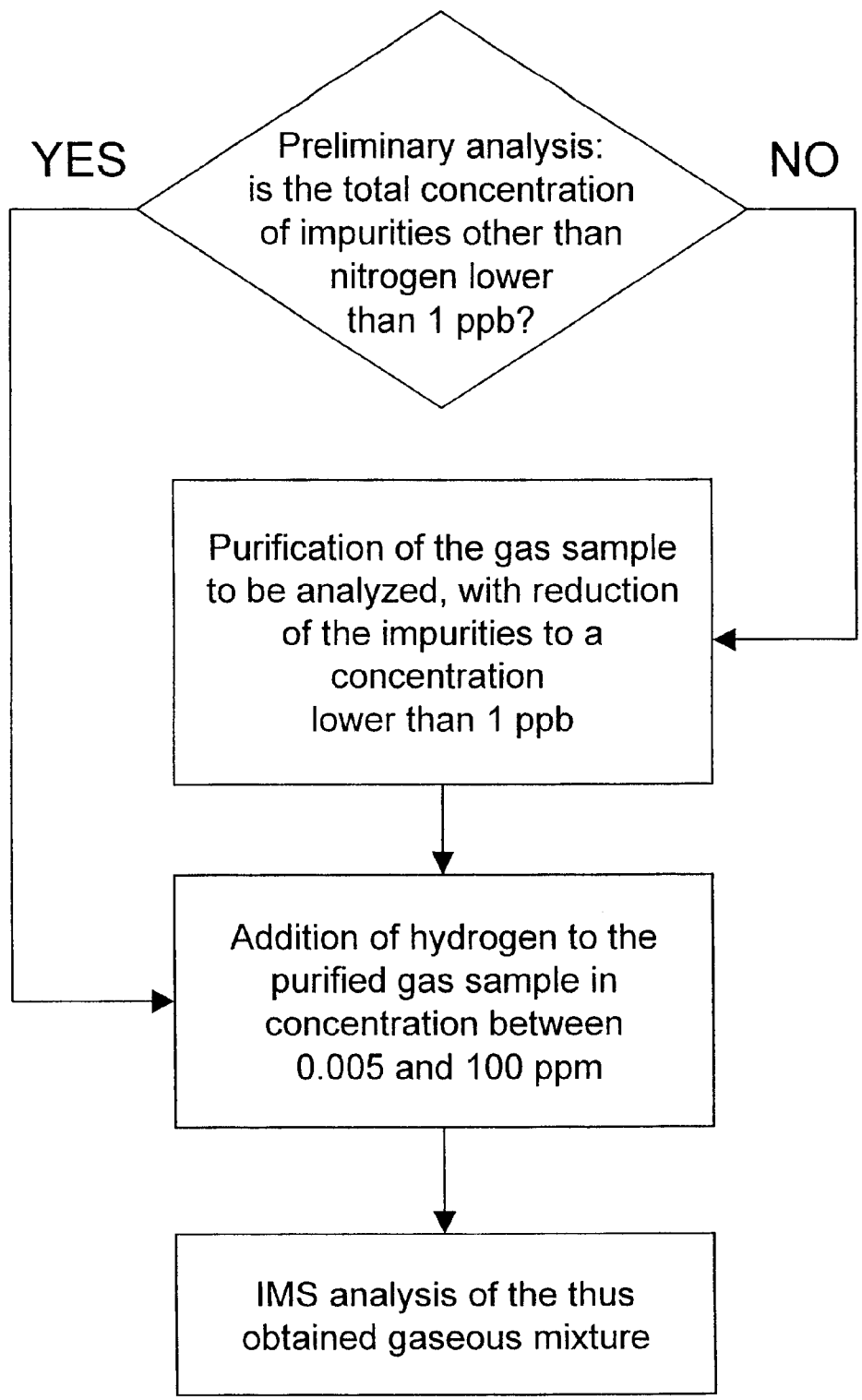
FIG. 2 is a flow diagram showing the essential steps of an alternative embodiment of the method of the invention.

FIG. 2 shows the steps of the method of the invention in an alternative embodiment thereof. In this second embodiment of the method, the argon flow to be analyzed is subjected to a preliminary analysis, run with the same IMS instrument, to assess the total content of impurities other than nitrogen. If the results of this trial analysis show that the total content of impurities in the original argon flow is already below 1 ppb, this flow is fed directly to the hydrogen addition step and actual analysis. If, on the other hand, the preliminary analysis shows that the total content of impurities (other than nitrogen) is higher than the above limit, the flow is passed through a purifier (or purification system) to bring the gas mixture composition in compliance with the requirements of the method of the invention.

Figure 3:
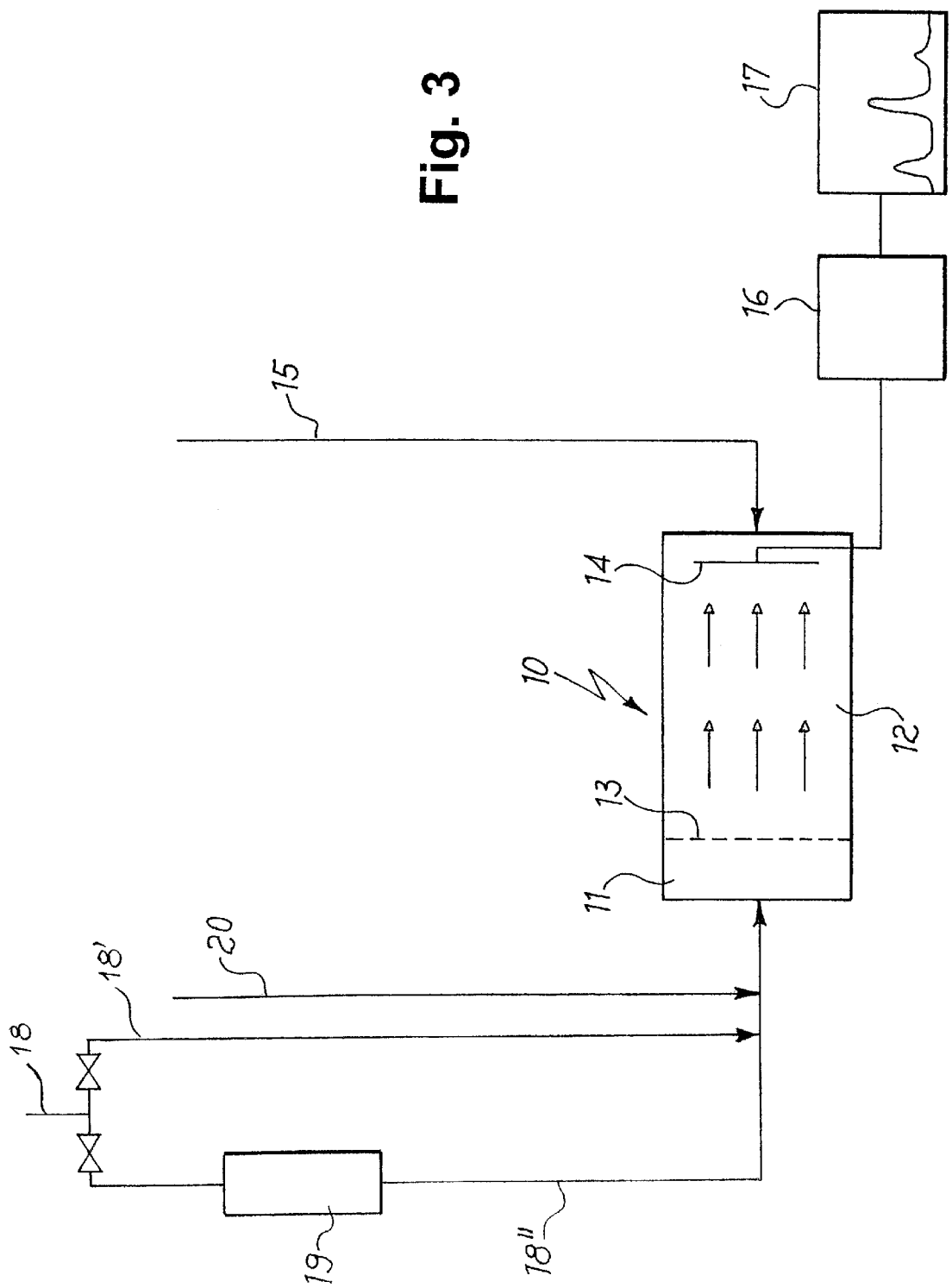
FIG. 3 is a schematic diagram of an EIS instrument for carrying out the method according to the invention.

FIG. 3 schematizes an IMS instrument for carrying out the second embodiment of the method according to the present invention. The actual IMS analyzer 10 has a ionization zone 11 and a separation zone 12 separated by grid 13. The gases introduced inside zone 11 are ionized by means of a radiation source, for example $^{63}$Ni (not shown in the FIG.); the so produced ions are introduced into zone 12 where, by means of electrodes (not shown) suitably placed along the walls of the same zone, they are accelerated towards detector 14; the motion of the ions in the separation zone is schematized in the drawing by the arrows. The velocity of motion towards the detector is slowed down due to the presence of argon in zone 12, which can either flow in a direction contrary to the motion of ions or be a static atmosphere (as described more in detail in the following). The instrument has a pure argon inlet position, deriving from line 15, on the side of the detector which is obviously necessary in the case that the analysis is carried out with the argon counter-flow. In the case that the analysis is carried out under a static argon atmosphere, line 15 is anyway necessary in order to allow cleaning of the separation zone between two subsequent analyses. Detector 14 is connected to an instrument 16, which converts the electrical signal generated on the detector to the spectrum 17 which represents the analysis result. The gas to be analyzed is introduced into the system through feeding line 18.

According to the second embodiment of the invention, the gas sample is subjected to a trial analysis If as a result of this trial test it is determined that the argon entering the system a through line 18 is pure enough, suitably acting on valves V1, V2, the flow is directed along line 18', undergoes hydrogen addition from line 20, and is sent to the analyzer 10. If the trial test determines that the argon in line 18 is not pure enough, suitably acting on valves V1, V2, the gas sample is passed through a purification station 19, capable of removing from the argon all gases or vapors other than nitrogen. Station 19 can be a single purifier or be formed of a series of more purifiers having different functionality. The so purified gas is sent along line 18", is added with hydrogen fed through line 20 and is then sent to the analyzer 10. Since for the purpose of the method of the invention it is necessary that the analyzed sample contains argon, nitrogen and hydrogen without impurities, gas lines 15 and 20 must in their turn come from suitably pure sources, or they must comprise further purification stations (not shown in the drawing). Besides, the metal lines 15, 18, 18', 18" and 20 are preferably made according to the usual techniques of pure gases technology, which generally involve the use of electropolished steel pipes in order to ensure extremely limited degassing from the internal walls of the same lines. In this embodiment the method of the invention may be operated according to a feed-back modality, connecting the EIS instrument to automated means (not shown) that control the valves so as to send the gas flow alternatively to the purifier or to the hydrogen addition step depending on the result of the IMS trial test. Valves V1 and V2 nay be replaced by any known method for directing a gas flow in a desired line out of a lines system.

A system for implementing the first embodiment of the method of the invention may be simply derived by the one shown in FIG. 3 by eliminating the derivation system comprising the valves (or equivalent means) and line 18'.

Whenever purification is effected, this must be carried out so as to guarantee that all the nitrogen present in the initial flow remains also in the purified flow, in order to avoid the quantitative measure of his gas being affected. It must be pointed out that the purifiers nowadays available are not able to completely remove the gases to be sorbed, and besides their purification features vary during their life. For the purposes of the present invention, the purifier must be able to guarantee that the residual quantity of impurities in the gas sample analyzed in the IMS is lower than 1 ppb. For the purposes of this disclosure, "sample of purified gas" or similar definitions may be understood to mean a gas sample having a total content of gases or vapors other than argon nitrogen or hydrogen lower than this limit. Preferably, the level of residual impurities in the purified sample is lower than 0.1 ppb. Suitable purifiers are, for example, nickel-based purifiers which work at room temperature and are able to sorb a broad variety of gases, particularly water, oxygen, carbon monoxide and dioxide and hydrogen, but are totally inert towards nitrogen. These purifiers are generally formed of metal nickel dispersed on a highly porous support, such as zeolites or a lumina. Preferred is the combination wherein a nickel-based purifier is preceded by a catalytic material for transforming some entering gases into species which can be more easily sorbed by nickel. For example, it is possible to use a bed of palladium oxide kept at a temperature between about 200 and 400° C., which is able to convert methane into carbon dioxide and water, which are then sorbed by the supported metallic nickel. Finally, these sorbing materials can be preceded by beds of other materials capable of physisorption of gases at room temperature, such as for example molecular sieves, which can remove part of the water, thus prolonging the life of the main nickel bed.

The method of the invention requires the addition of hydrogen to the argon flow possibly purified as described above. As said, hydrogen is added with the purpose of forming the ArH$^+$ ion, which is capable of transferring the charge to a nitrogen molecule, thus forming the N$_2$H$^+$ ion, the species effectively detected in the analysis. It has been found that, in order to obtain a reliable and reproducible measures of the quantity of nitrogen in argon, hydrogen must be present in the mixture of gas subjected to the analysis in amount of at least 0.005 ppmv. The upper limit of said quantity is not rigidly fixed, and could reach about 100 ppmv. In the case that the instrument is used also for analyses other than those of nitrogen in argon, the use of high quantities of hydrogen involves longer cleaning times before passing to another analysis, so that it can be preferable to add hydrogen in quantities such that the concentration thereof in the mixture subjected to analysis is lower than about 0.2 ppmv, and preferably of about 0.1 ppmv. These concentrations can be obtained by mixing in suitable ratios the argon flow, possibly coming from the purification step, with a mixture containing hydrogen in argon Alternatively, it is possible to use mixtures containing hydrogen in helium, because this latter gas cannot be detected in an IMS analysis, and therefore does not interfere with it. These hydrogen/argon or hydrogen/helium mixtures are commercially available in cylinders from pure gas suppliers at prefixed concentrations. As an example, by using a hydrogen/argon mixture with 1 ppmv of hydrogen, the concentration of 0.1 ppmv of hydrogen in the gas sample which is sent to the IMS analysis is obtained by mixing the argon to be analyzed and the hydrogen/argon mixture in a ratio of 9:1.

Obviously, it is necessary that the addition of hydrogen introduces no impurities into the mixture. In the case that the ratio between the argon flow to be analyzed and the mixture containing hydrogen is high, for example higher than 1000, it is possible to assume that the addition of hydrogen introduces no impurities because in commercial mixtures containing hydrogen the impurities am generally present at levels lower than a ppm, and with high dilution their level becomes negligible. On the contrary, in case the ratio is lower than 1000, and particularly when it is lower than 500, it can be preferable to also purify the mixture containing hydrogen with suitable purifiers, in particular with water removing systems. For this purpose, it is possible to use purifiers of the type using water chemical sorption based on the use of an oxide of a earth-alkali metal selected from the group consisting of calcium, strontium and barium, or of the type using physical sorption, such as molecular sieves.

The addition of hydrogen to the mixture to be analyzed can also be carried out by means of hydrogenated non-evaporable getter alloys (known in the field as NEG alloys). The NEG alloys are widely used in the art to maintain the vacuum or for removing traces of reactive gases from flows or environments of inert gases. As blown, these alloys irreversibly sorb species such as water, oxygen or carbon oxides. On the contrary, the sorption of hydrogen is reversible, and the gas sorbed at relatively low temperatures can then be released by increasing the temperature of the alloy. Each NEG alloy presents, at any given temperature, a characteristic equilibrium pressure of free hydrogen. It is therefore possible to carry out the addition of hydrogen to the mixture to be analyzed with IMS by using a NEG alloy "charged" with hydrogen and maintained at a suitable temperature, and allowing pure argon or helium to flow over it. By suitably regulating the temperature of the alloy and the noble gas flow, it is possible to obtain a mixture of hydrogen in argon or helium having the desired hydrogen concentration. This way offers the advantage that the so obtained mixture certainly has the purity features which are necessary for the method according to the invention. For an illustration of the principles for charging the NEC alloys with hydrogen and removing therefrom the gas in equilibrium conditions (which are outside of the objects of the present invention), European patent EP-B-716772 in the name of the applicant is referred to The so obtained mixture, containing only argon, nitrogen and hydrogen, is introduced into the ionization chamber of the IMS instrument and can be analyzed according to the typical procedure of this technique, that is by employing in the separation zone of the IMS instrument a flow of a gas which does not interfere with the measure having direction contrary to the travelling direction of the ions. This counter-current of gas is indicated in the field as "drift gas," and preferably consists in a flow of purified gas corresponding to the main gas in the analysis (in this case, argon).

In the particular case of the present invention, it has been found that the analysis can also be effected by operating without an argon drift. This alternative operative procedure, if applied to analyses other than the one object of the present invention yields a clear worsening of the results with respect to the standard procedure with the drift gas. On the contrary, in the specific case of the analysis of nitrogen in argon according to the present invention, it has been found that this operative procedure may be employed for obtaining good analysis results. In particular, it has been found that by operating with the standard mode (i.e. with drift gas) the signal read by the detector corresponding to the different ions present comes more readily to an equilibrium, thus allowing a more rapid analysis; on the other hand, it has been found that analyzing the nitrogen content in argon by operating without the argon drift enhances the sensitivity towards nitrogen, thus increasing the analytical capabilities of the method. The preferred operating mode is then to be decided depending on whether in the analysis it is preferred to have a quick response, or it is preferred to have the possibility of detecting lower amounts of nitrogen. It is also possible to combine the two operating modes, by first carrying out a "quick" analysis (with argon drift) and, if no nitrogen is detected, to resort to the nodrift method to confirm absence of nitrogen or to detect very low amounts of this gas.

The invention will be further illustrated by the following examples. In all the following tests (both tests representative of the invention method, and comparative tests which are not representative of the method) the flow of gaseous mixture entering the analyzer is kept equal to 0.5 liters per minute. The ionization of the sample is carried out by means of a radioactive source of $^{63}$Ni. The ions formed are neutralized On the grid until the potential thereof is annulled, thus allowing their entrance into the separation zone; the time of annulment of the grid potential s of 200 microseconds ($\mu$s) in each test. The tests of the following examples are carried out with an IMS instrument having a separation zone 8 cm long; in au the tests the acceleration electrical field is equal to 128 V/cm. From indicative preliminary tests, it has been found that under these conditions the typical times of flight of the species present in the tests are generally between 15 and 30 milliseconds (ms); in particular, the time of flight of the $N_2H$ ion is about 20 ms. The results of all the tests of the examples are given in graphs showing peaks of height corresponding to the concentration of a given ion as a function of the time of flight thereof The intensity of the peaks is given in volts (V); the transformation of the current directly measured by the detector (number of ions which collide on the detector per unit of time) in volts is operated by the instrument electronic system. In all the graphs (except FIGS. 3.$a$ and 4.$a$, enlarged views of details of main graphs) there is indicated, in correspondence with each peak, the corresponding ion.

EXAMPLE 1

Six tests are carried out in order to evaluate the efficacy of the method according to the invention in detecting traces of nitrogen (in concentrations in the ppb range) in argon.

The first test is carried out by sending to the analysis argon containing no nitrogen, whereas in tests 2 to 6 argon/nitrogen mixtures containing increasing quantities of nitrogen are analyzed, up to a maximum of 15 ppb. AU these tests are carried out with a static argon atmosphere in the separation zone of the IMS instrument (no drift condition).

In all the tests (included the one with pure argon), the sample gas is purified before the analysis by putting it through a two-step purifier of which the first is formed of a PdO bed kept at 250° C., and the second is of nickel metal kept at room temperature on silica After the purification, the gas is added with an argon/hydrogen mixture in a flow ratio such that in the resulting mixture the concentration of hydrogen is always 50 ppb. The following table reports the inlet concentration of nitrogen in each test:

TABLE 1

| Test | Nitrogen concentration (ppb) |
|---|---|
| 1 | 0 |
| 2 | 3 |
| 3 | 6 |
| 4 | 9 |
| 5 | 12 |
| 6 | 15 |

Figure 4:
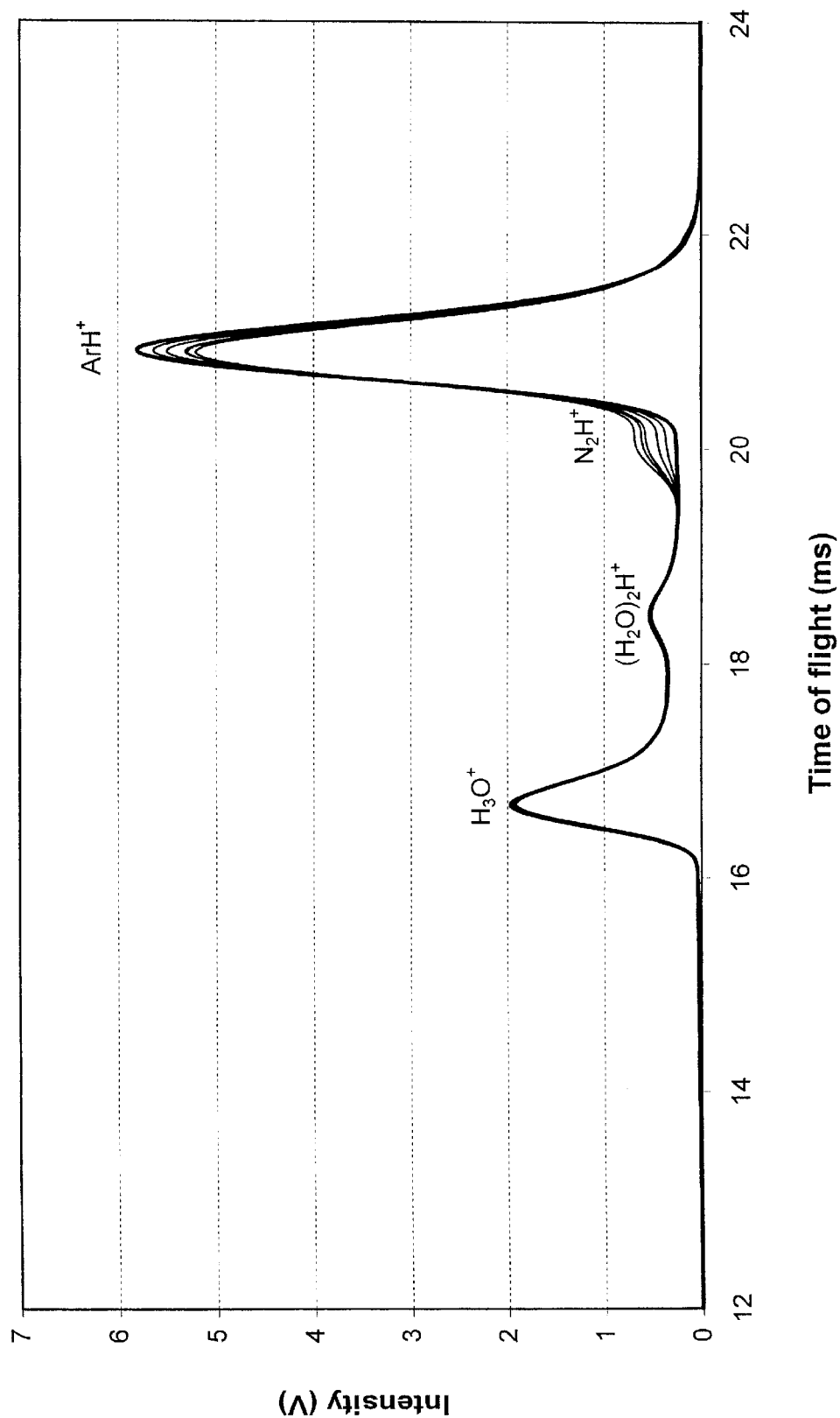
FIGS. 4 to 9 are graphs showing results of IMS analyses of nitrogen in argon carried out according to the embodiments of the invention and comparative tests.

The result of the six tests are given in a graph in FIGS. 4 and 4.$a$. FIG. 4 shows the complete plot of the six tests; the peaks at about 16.5 and 18.5 ms are attributed to the species $H_3O^+$ and $(H_2O)_2H^+$ respectively. The presence of these two species is due to a residual concentration of about 0.7 ppb of water, which can derive from the degassing of the walls of the instrument itself or of the pipes, or from a non perfect removal by the purifier. This value of about 0.7 ppb of water represent a practically unavoidable "background" at the conditions of the tests. The peak of the species $N_2H^+$ appears at a time of flight of about 20 ms as a shoulder on the main peak corresponding to $ArH^+$ ion. An enlarged view of the graph of FIG. 4, centered at 20 ms, is reported in FIG. 4.a, and shows the detail of the relevant zone for the analysis centered around the peak of the species $N_2H^+$. The numbers of the curve in FIG. 4.a correspond to a test number reported in Table 1. It can be seen that the intensity of the peak of the species $N_2H^+$ increases in a monotonous way as the nitrogen concentration increases. In FIG. 4, with the increase of the $N_2H^+$ peak corresponds a regular decrease in the intensity of the $ArH^+$ peak (for the sake of clarity, the curves in FIG. 4 are not numbered, but the $ArH^+$ peak is at a maximum in the case of curve 1, showing absence of nitrogen, whereas curve 6 representing the maximum concentration of nitrogen corresponds to the minimum height of the $ArH^+$ peak).

EXAMPLE 2

In this example the difference of efficacy of the method according to the invention depending on whether or not an argon drift is established in the separation zone is evaluated.

The two tests are carried out with purification of the sample gas as described for Example 1, by sending to the analysis a gaseous mixture containing 15 ppb of nitrogen and 25 ppb of hydrogen. In test 7 an argon drift is not established in the separation zone of the IMS instrument, whereas in test number 8 in said zone there is a counter-flow of argon of 0.25 liters/minute.

Figure 5:
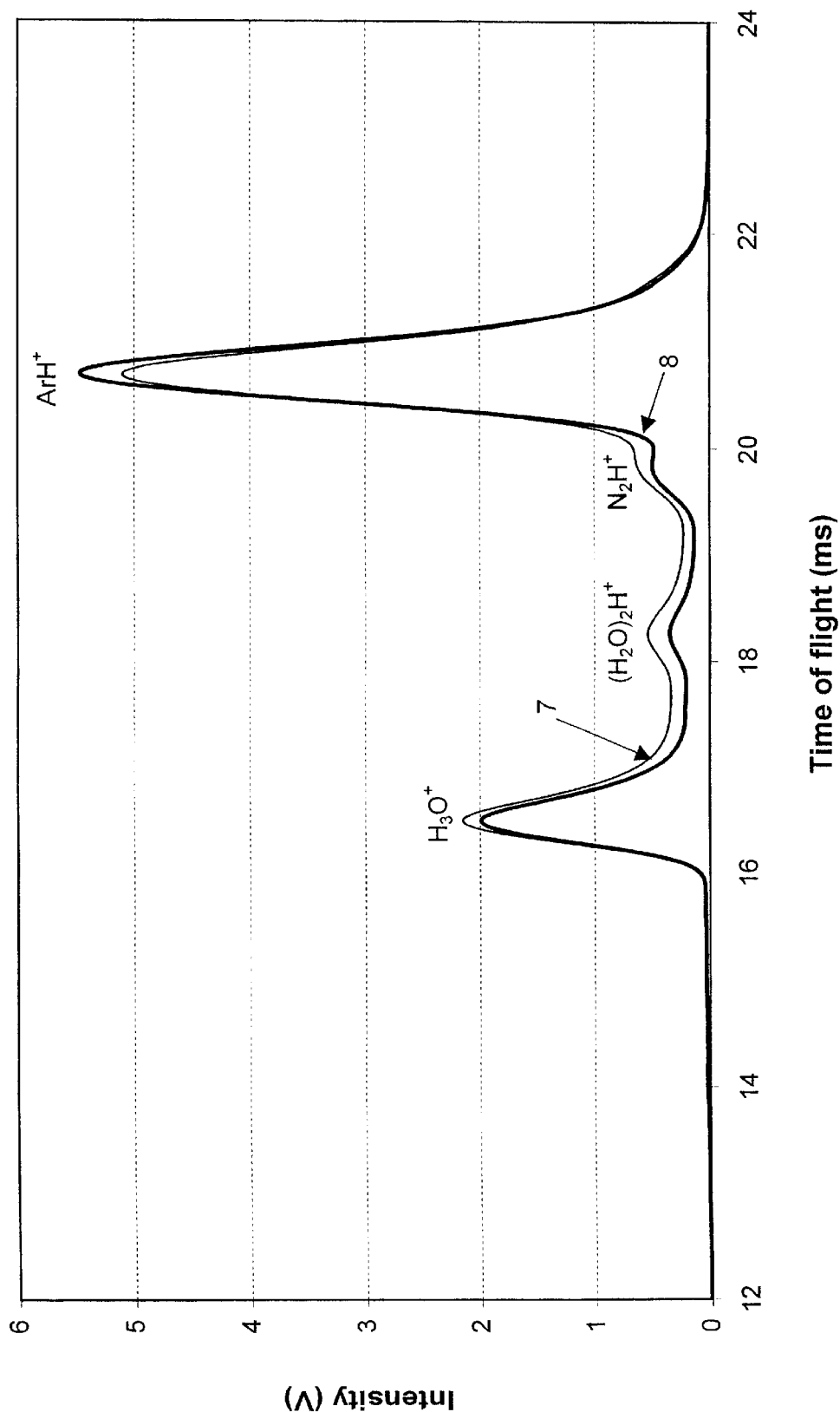

The test results are reported in FIGS. 5 and 5a. Also in this case, there are peaks corresponding to $H_3O^+$ and $(H_2O)_2H^+$. The notable result (more evident in FIG. 5.a) is that in test 7 (without counter-flow) there is an increase of the intensity of the peak relevant to ion N2H+ with respect to that which is obtained in test 8, with argon drift.

EXAMPLE 3 (COMPARATIVE)

An IRS analysis is carried out on a mixture containing 10 ppb of nitrogen and 2 ppb of hydrogen in argon. The initial sample (argon/nitrogen mixture plus impurities) is subjected to a purification treatment as in Example 1, but the hydrogen concentration is lower than the minimum amount required according to the invention.

Figure 6:
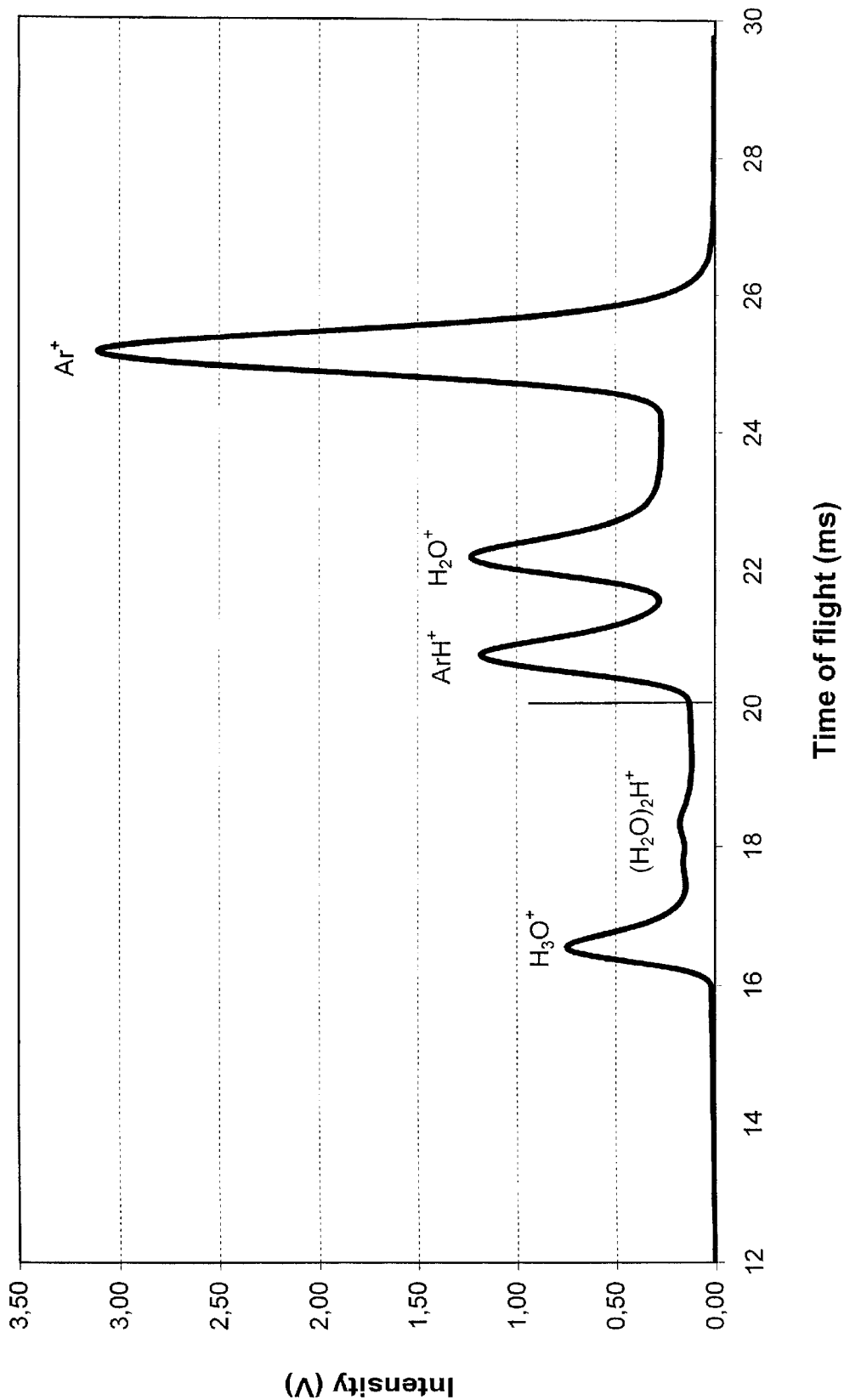

The results of the test are reported in FIG. 6; it can be seen that peaks due to the presence of trace water (lower than 1 ppb) are present, whereas at the time of flight of about 20 ms (marked by the vertical segment) the peak corresponding to the ion $N_2H^+$ does not appear.

EXAMPLE 4 (COMPARATIVE)

The effect of traces of $CO_2$ on the analysis of nitrogen in argon is evaluated. For evaluating the effect of a single impurity, a mixture containing nitrogen in argon is first purified according to the procedure of Example 1, and subsequently added with hydrogen and $CO_2$ in suitable concentrations. Three different mixtures of gases so produced are subjected to IMS analysis with no argon drift in the separation zone. The analyzed mixtures in the three tests are formed of argon (main gas) containing 500 ppb of nitrogen, 500 ppb of hydrogen and the following concentration of $CO_2$:

test 9: 0 ppb;
test 10: 3 ppb
test 11: 9 ppb.

Figure 7:
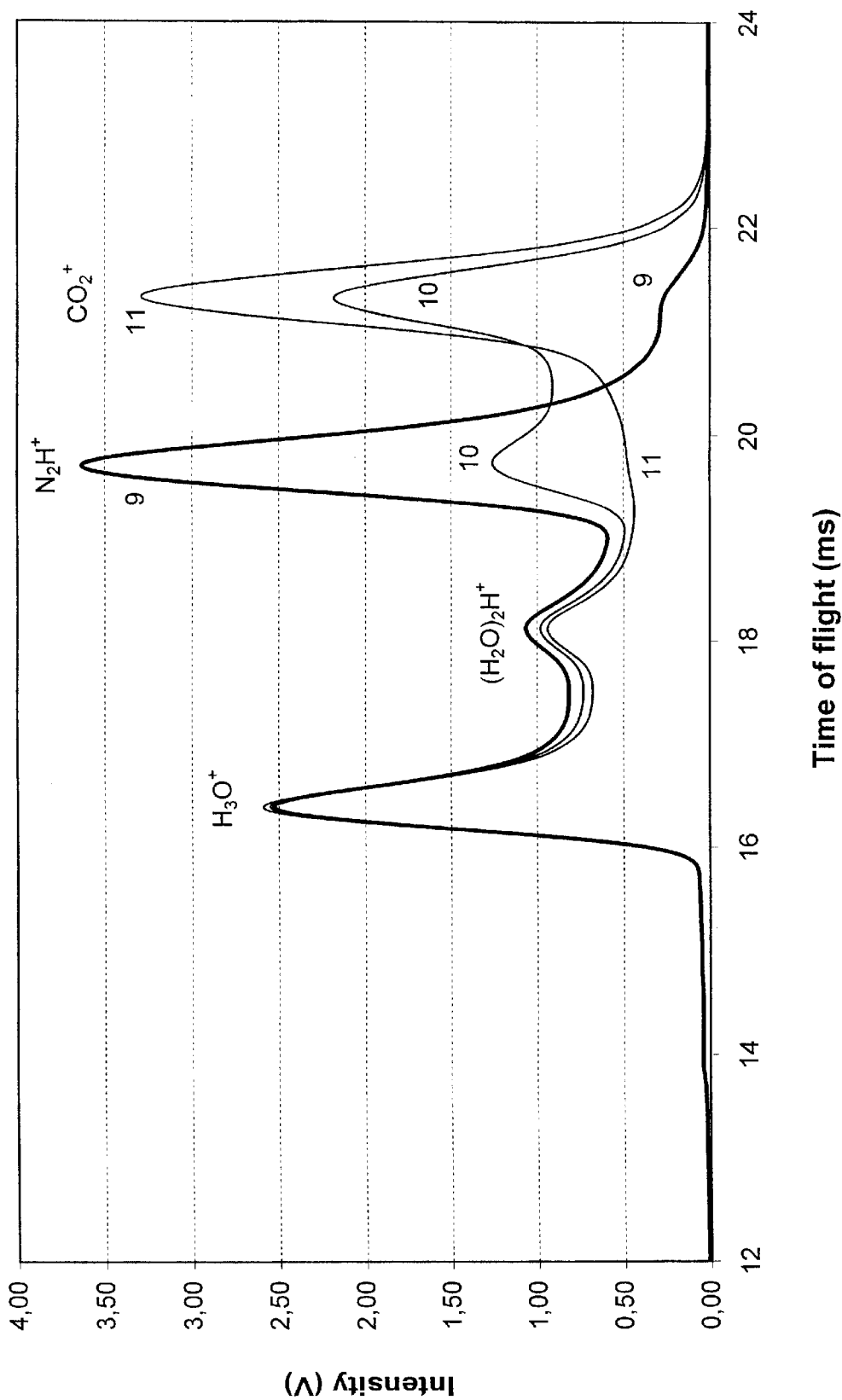

The results of the three tests are reported in a graph in FIG. 7. The peak of $ArH^+$ is not present in the curves because, with 500 ppb of nitrogen and hydrogen, the transfer of the charge from $ArH^+$ to nitrogen is total. The curve relevant to test 9 (without addition of $CO_2$) show a strong peak corresponding to the $N_2H^+$ ion. With 3 ppb of $CO_2$ this becomes the preferred species for receiving the charge transferred from $ArH^+$ (curve 10) and already in these conditions the intensity of the ion $N_2H^+$ peak notably decreases. With 9 ppb of $CO_2$, that is a concentration of about 1/50 of the nitrogen present, the peak corresponding to $N_2H^+$ disappears (curve 11).

EXAMPLE 5 (COMPARATIVE)

The effect of traces of methane on the analysis of nitrogen in argon is evaluated. Three tests are carried out (with the same procedure of Example 4). The content of $CH_4$ in the analyzed mixtures in the three tests is:

test 12: 0 ppb;
test 13: 3 ppb;
test 14: 9 ppb

Figure 8:
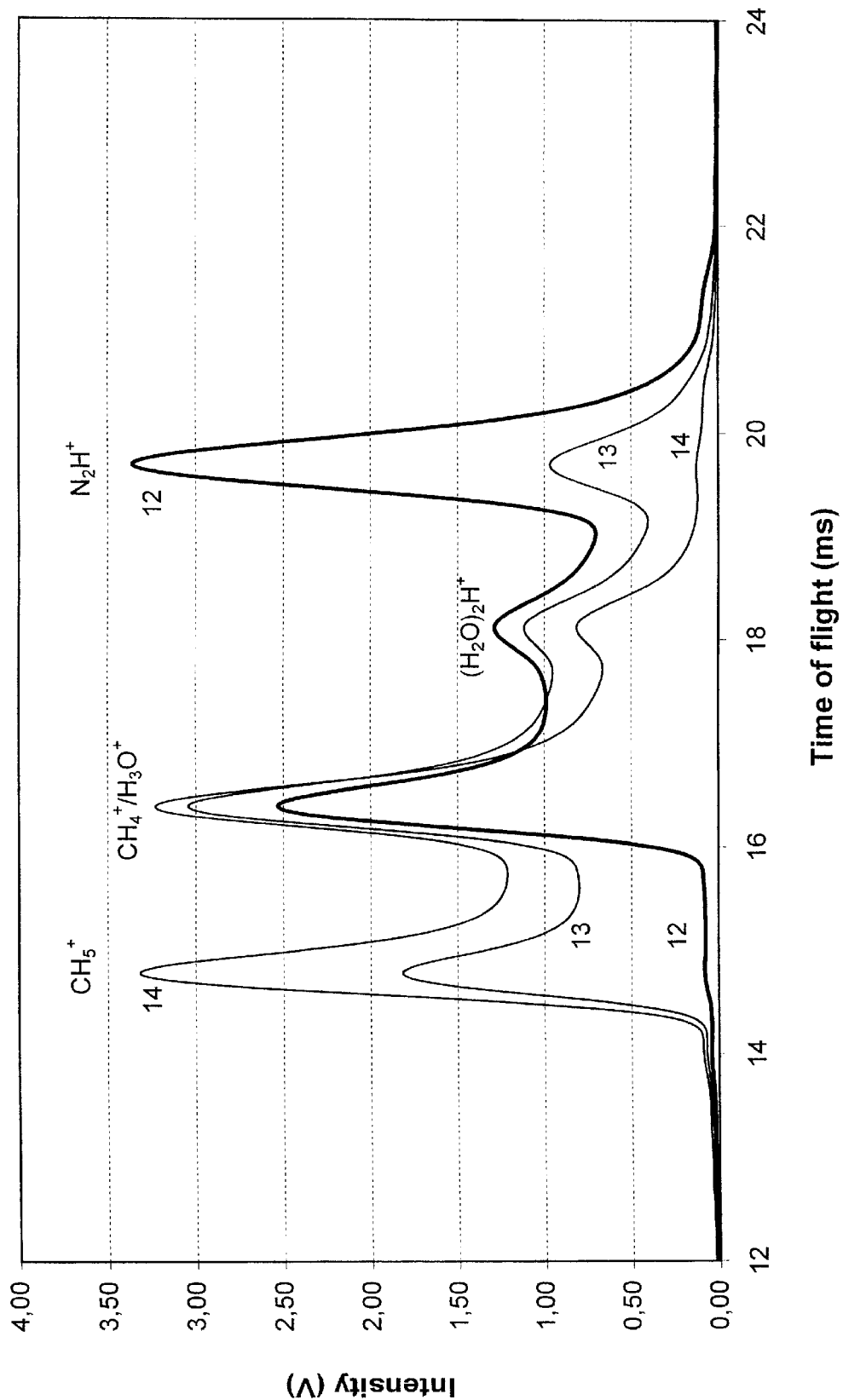

The results of the three tests are reported in a graph in FIG. 8. The curve relevant to test 12 (without methane added) shows an intense peak corresponding to the ion $N_2H^+$. With 3 ppb of $CH_4$ (curve 13) the charge transfer by $ArH^+$ takes place mainly in favor of the methane (peak at about 15 ms) and the intensity of the peak of the ion $N_2H^+$ notably decreases. With 9 ppb of $CH_4$ (curve 14), that is a concentration which is about 1/50 of that of nitrogen, the peak corresponding to $N_2H^+$ has practically disappeared.

EXAMPLE 6 (COMPARATIVE)

The effect of traces of water, intentionally added in concentrations higher than 1 ppb, on the analysis of nitrogen in argon is evaluated. Three tests are carried out (with the same procedure of Example 4). The content of $H_2O$ intentionally added in the analyzed mixture in the three tests is:

test 15: 0 ppb;
test 16: 2 ppb;
test 17: 5 ppb.

Figure 9:
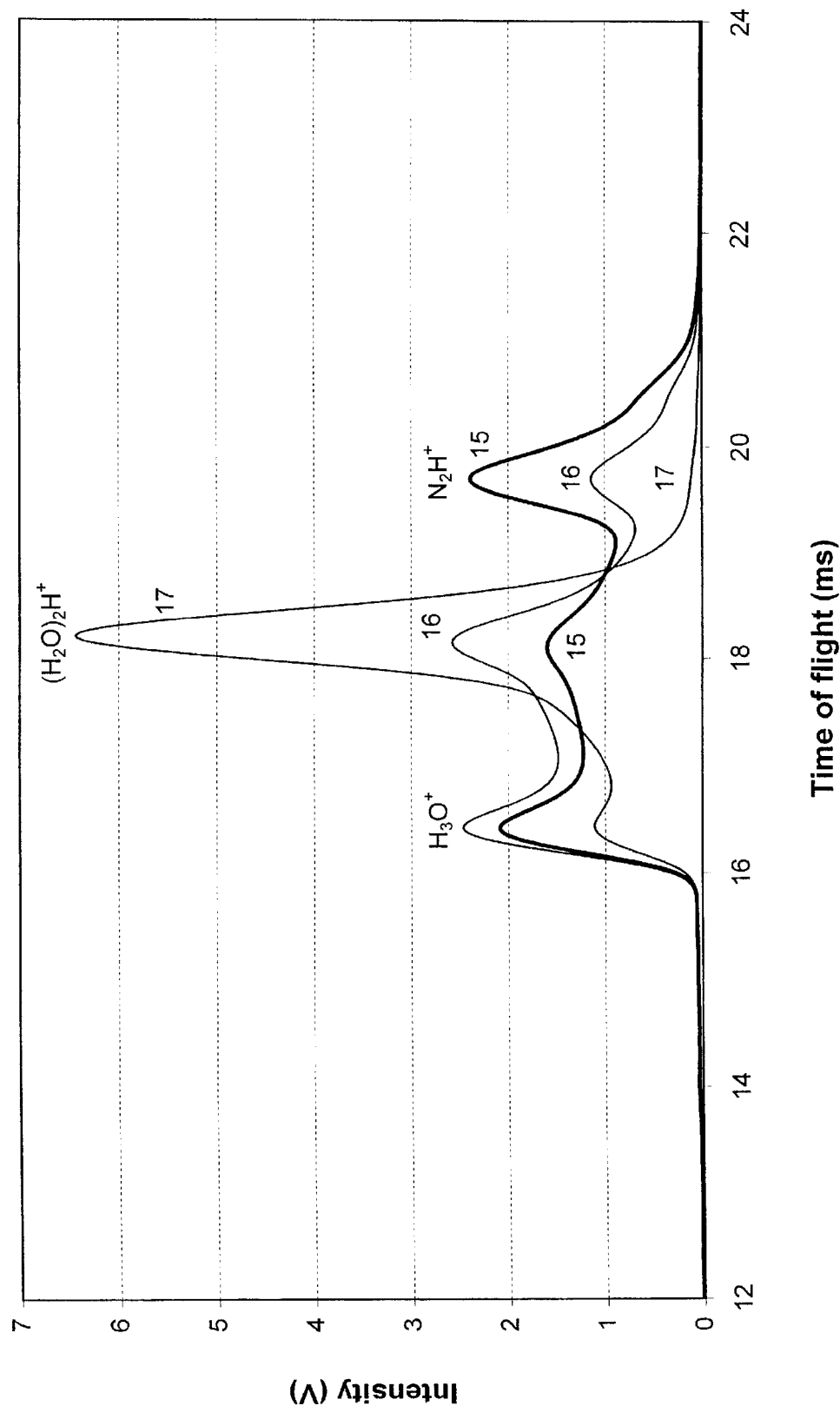

The results of the three tests are reported in graph in FIG. 9. In the curve relevant to test 15, obtained without intentionally added water, the peak corresponding to the ion $N_2H^+$ is the one having greater intensity. With 2 ppb of $H_2O$ (curve 16) the two peaks corresponding to the ions $H_3O^+$ and $(H_2O)_2H^+$ become dominant and the intensity of the $N_2H^+$ peak is reduced to one half of that of curve 15. Finally, with 5 ppb of $H_2O$, that is a concentration of 1/100 with respect to that of the present nitrogen, the peak of $N_2H^+$ completely disappears.

As proved by means of the results of the reported examples, with the method according to the invention it is possible to carry out the IMS analysis of traces of nitrogen in argon. In particular, the method of analysis is capable of detecting 3 ppb of nitrogen in argon and of easily discriminating different nitrogen concentrations in the range of concentrations form 3 to 15 ppb (FIGS. 4 and 4.a). Further, unusual in IMS analyses, in this case the sensitivity of the method can be increased by operating without a pure argon drift in the separation zone of the IMS instrument (FIGS. 5 and 5.a). FIG. 6 demonstrates the necessity of adding hydrogen, without which it is not possible to detect nitrogen in argon in concentrations which are instead easily detectable by operating according to the invention. FIGS. 7–9 demonstrate finally that levels of impurities on the order of 2–3 ppb are sufficient for dramatically reducing the sensitivity of an IMS analysis in nitrogen detection, thus compromising the possibility to effect quantitative analysis. Further, with concentrations of 1 ppb of water (1/100 of the nitrogen concentration) or around 10 ppb (1/50 of the nitrogen concentration) in the case of other impurities, the possibility to carry out the simple qualitative analysis of nitrogen in argon with the IMS method is also lost.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for measuring nitrogen concentration in argon by means of ionization mobility spectroscopy comprising the steps of:

providing an argon flow sample to be analyzed comprising a total concentration of impurities other than nitrogen not higher than about 1 ppb;

adding a quantity of hydrogen to the argon flow sample to be analyzed to produce a mixture of gases comprising a hydrogen concentration between 0.005 and 100 parts per million by volume; and analyzing the so produced mixture of gases with an IMS analyzer to determine the concentration of nitrogen in argon.

2. A method according to claim 1 wherein the argon flow with total concentration of impurities other than nitrogen not higher than about 1 ppb is provided by passing said flow through a purifier or a system made up of more purifiers or purification beds.

3. A method according to claim 1 wherein the argon flow with total concentration of impurities other than nitrogen not higher than about 1 ppb is provided by effecting a preliminary IMS analysis of the argon flow to determine whether said total concentration of impurities is higher than 1 ppb, and if said total concentration is higher than 1 ppb, passing the argon flow through a purifier or a system made up of purification beds, while if said total concentration is not higher than 1 ppb, directly effecting the addition of hydrogen to the flow.

4. A method according to claim 3 operated according to a feed-back modality, by connecting an IMS instrument to automated means, that depending on the output of the preliminary analysis, is capable of controlling the direction of the gas flow in at least two different lines of a gas lines system, wherein at least one of said lines comprises a gas purifier or purification system and at least another line does not comprise such purifier or purification system.

5. A method according to claim 1 wherein said impurities content is lower than 0.1 ppb.

6. A method according to claim 1 wherein the purification step is carried out by employing a purifier based on nickel metal kept at room temperature.

7. A method according to claim 6 wherein the purifier comprises metallic nickel dispersed on a porous support.

8. A method according to claim 6 wherein upstream the purifier based on metallic nickel is employed a bed of a palladium oxide kept at a temperature between about 200 ° C. and 400 ° C.

9. A method according to claim 6 wherein upstream the purifier based on metallic nickel is employed a bed material capable of sorbing water vapor at room temperature.

10. A method according to claim 9 wherein such water sorbing material is molecular sieves.

11. A method according to claim 1 wherein the hydrogen concentration is about 0.2 ppm.

12. A method according to claim 11 wherein said concentration is about 0.1 ppm.

13. A method according to claim 1 wherein the step of additioning hydrogen to the sample of purified gas is carried out by mixing in suitable ratio a flow of the purified sample gas and a flow of a hydrogen/argon or hydrogen/helium mixture.

14. A method according to claim 13 wherein, when the ratio between the flow of argon to be analyzed and the flow of hydrogen/argon or hydrogen/helium mixture is lower than 1000, said mixture is purified with a system of water removal.

15. A method according to claim 14 wherein molecular sieves or an oxide of a alkali-earth metal selected among calcium, strontium or barium are employed in said system of water removal.

16. A method according to claim 1 wherein the step of additioning hydrogen to the sample of purified gas is carried out by flowing argon or helium on a hydrogenated non-evaporable getter alloy kept at suitable temperature, and additioning the so obtained mixture of hydrogen in noble gas to be the gas mixture to be analyzed.

17. A method according to any of the preceding claims wherein the analysis step is carried out by establishing in the separation zone of the IMS instrument a flow of pure argon contrary to the direction of motion of the ions.

18. A method according to any of claims 1 to 16 wherein the analysis step is carried out by using static argon in the separation zone of the IMS instrument.

* * * * *